US006492577B1

(12) United States Patent
Harada et al.

(10) Patent No.: US 6,492,577 B1
(45) Date of Patent: Dec. 10, 2002

(54) LEAFY COTYLEDON2 GENES AND THEIR USES

(75) Inventors: John Harada, Davis, CA (US); Linda Kwong, Sacramento, CA (US); Kelly Matsudaira Yee, Antelope, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/527,058

(22) Filed: Mar. 16, 2000

(51) Int. Cl.⁷ .................. C07H 21/04; C07H 15/87; A01H 11/00; A01H 5/00; C12N 5/04; C12N 15/82; C12N 15/74

(52) U.S. Cl. ............... 800/290; 800/287; 800/278; 800/298; 536/23.1; 536/24.1; 536/23.6; 435/419; 435/468

(58) Field of Search ................... 800/290, 294, 800/298, 295, 287, 278; 536/23.1, 23.6, 24.1; 435/468, 419; 530/372

(56) References Cited

FOREIGN PATENT DOCUMENTS

WO    WO 98/37184    8/1998

OTHER PUBLICATIONS

Broun et.al.; Catalytic Plasticity of Fatty Acid Modification Enzymes Underlying Chemical Diversity of Plant Lipids, 1998, Science, vol. 282: 1315–1317.*

Hill et. al.; Functional Analysis of Conserved Histidines in ADP–Glucose Pyrophosphorylase from Escherichia Coli, 1998, Biochemical and Biophsysical Research Communications 244: 573–577.*

Izawa et. al.; Plant bZIP Protein DNA Binding Specificity, 1993, J. Moi. Biol. 230: 1131–1144.

Bowie et.al.; Deciphering the Message in Protein Sequences: Tolerance to Amino Acid Substitutions, 1990, Science, vol. 247:1360–1310.

Burgess et.al.; Possible Dissociation of the Heparin–binding and MitogenicActivities . . . by Site–directed Mutagenesis of a Single Lysine Residue, 1990, Journal of Cell Biology, vol. 111: 2129–2138.

Lazar et.al.; Transforming Growth Factor: Mutation of Aspartic Acid 47 and Leucine 48 Results in Different Biological Activities, 1988, Molecular and Cellular Biology: 1247–1252.

Lohmann et.al.; A Molecular Link between Stem Cell Regulation and Floral Patterning in Arabidopsis, 2001, Cell, vol. 105: 793–803.

Busch et.al.; Activation of a Floral Homeotic Gene in Arabidopsis, 1999, Science, vol. 285: 585–587.

Stone et.al.; Leafy Cotyledon2 encodes a B3 domain transcription factor that induces embryo development, 2001, PNAS, vol. 98, No. 20:11806–11811.

Hao et.al.; Unique Mode of GCC Box Recognition by the DNA–binding Domain of Ethylene–responsive Element–binding Factor (ERF Domain) in Plant, 1998, Journal of Biological Chemistry, vol. 273,No. 41: 26857–26861.

West, et al., "Leafy Coyledon1 Is An Essential Regulator of Late Embryogenesis and Cotyledon Identity in Arabidopsis"; *The Plant Cell*, vol. 6, 1731–1745 (Dec. 1994).

Meinke, et al., "Leafy Cotyledon Mutants of Arabidopsis"; *The Plant Cell*, vol. 6, 1049–1064 (Aug. 1994).

Baumlein, et al., "The FUS3 Gene of *Arabidopsis thaliana* is a regulator of gene expression during late embryogenesis,"; *The Plant Journal*, 6(3): 379–387 (1994).

Becker, et al., "A cDNA encoding a human CCAAT–binding protein cloned by functional complementation in yeast"; *Proc. Natl. Acad. Sci. USA*, vol. 88:1968–1972 (Mar. 1991).

Sinha, et al., "Recombinant rat CBF–C, the third subunit of CBF/NFY, allows formation of a protein–DNA complex with CBF–A and CBF–B and with yeast HAP2 and HAP3"; *Proc. Natl. Acad. Sci. USA*, vol. 92, 1624–1628 (Feb. 1995).

Li, et al., "Evolutionary variation of the CCAAT–binding transcription factor NF–Y"; *Nucleic Acids Res.*, vol. 20, No. 5, 1087–1091 (Feb. 1992).

Johnson, et al., "Eukaryotic Transcriptional Regulatory Proteins"; *Annu. Rev. Biochem.*, 58:799–839 (1989).

Xing, et al. "Mutations in yeast HAP2/HAP3 define a hybrid CCAAT box binding domain"; *The EMBO J.*, vol. 12, No. 12, 4647–4655 (1993).

McCarty, et al., "The Viviparous–1 Developmental Gene of Maize Encodes a Novel Transcriptional Activator"; *Cell*, vol. 66, 895–905 (Sep. 1991).

McCarty, D., "Genetic Control and Integration of Maturation and Germination Pathways in Seed Development"; *Annu. Rev. Plant Physiol. Plant Mol. Biol.*, 46:71–93 (1995).

Giraudat, J., "Abscisic acid signaling"; *Current Opinion in Cell Biology*, 7:232–238 (1995).

Parcy, et al., "Regulation of Gene Expression Programs during Arabidopsis Seed Development: Role of the AB13 Locus and Endogenous Abscisic Acid"; *The Plant Cell*, vol. 6, 1567–1582 (Nov. 1994).

McCarty, et al., "Molecular Analysis of viviparous–1: An Abscisic Acid–Insensitive Mutant of Maize"; *The Plant Cell*, vol. 1, 523–532 (May 1989).

Heck, et al., "AGL15, a MADS Domain Protein Expressed in Developing Embryos"; *The Plant Cell*, vol. 7, 1271–1282 (Aug. 1995).

(List continued on next page.)

*Primary Examiner*—Elizabeth F. McElwain
*Assistant Examiner*—Stuart Baum
(74) *Attorney, Agent, or Firm*—Townsend and Townsend and Crew LLP

(57) ABSTRACT

The present invention provides nucleic acid sequences from embryo-specific genes. The nucleic acids are useful in targeting gene expression to embryos or in modulating embryo development.

57 Claims, 1 Drawing Sheet

OTHER PUBLICATIONS

Valvekens, et al., "*Agrobacterium tumefaciens*–mediated transformation of *Arabidopsis thaliana* root explants by using kanamycin selection"; *Proc. Natl. Acad. Sci., USA*, vol. 85, 5536–5540 (Aug. 1988).

Ming–Tsair Chan, et al., "Novel Gene Expression System for Plant Cells Based on Induction of α–Amylase Promoter by Carbohydrate Starvation"; *The Journal of Biological Chemistry*, vol. 269, No. 26, 17635–17641 (Jul. 1994).

Shimada, et al., "Antisense regulation of the rice waxy gene expression using a PCR–amplified fragment of the rice genome reduces the amylose content in grain starch"; *Theoretical and Applied Genetics*, vol. 86, 665–672 (Jan. 1993).

Meinke, David, "A Homoeotic Mutant of *Arabidopsis thaliana* with Leafy Cotyledons"; *Science*, vol. 258, 1647–1650, (Dec. 1992).

Keith, K., et al. "fusca3: A Heterochronic Mutation Affecting Late Embryo Development in Arabidopsis," *Plant Cell* 6:589–600 (May 1994).

Lotan, T., et al. "Arabidopsis Leafy Cotyledon1 Is Sufficient to Induce Embryo Development in Vegetative Cells," *Cell* 93: 1195–1205 (Jun. 1998).

LuerBen, H., et al. "Fusca3 encodes a protein with a conserved VP1/ABI3–like B3 domain which is of functional importance for the regulation of seed maturation in *Arabidopsis thaliana*," *The Plant Journal* 15(6):755–764 (1998).

Parcy, F., et al. "The Abscisic Acid–Insensitive3, Fusca3, and Leafy Cotyledon1 Loci Act in Concert Control Multiple Aspects of Arabidopsis Seed Development," *The Plant Cell* 9:1265–1277 (Aug. 1997).

Suzuki, M., et al. "The Conserved B3 Domain of Viviparous1 Has a Cooperative DNA Binding Activity," *The Plant Cell* 9:799–807 (May 1997).

Federspiel, N.A., et al. "A thaliana chromosome 1 BAC F3H9 genomic sequence" Database EM_PL Online EMBL; Jan. 14, 2000 Database accession No. AC021044 XP002182632 abstract.

* cited by examiner

US 6,492,577 B1

LEAFY COTYLEDON2 GENES AND THEIR USES

FIELD OF THE INVENTION

The present invention is directed to plant genetic engineering. In particular, it relates to new embryo-specific genes useful in improving agronomically important plants.

BACKGROUND OF THE INVENTION

Embryogenesis in higher plants is a critical stage of the plant life cycle in which the primary organs are established. Embryo development can be separated into two main phases: the early phase in which the primary body organization of the embryo is laid down and the late phase which involves maturation, desiccation and dormancy. In the early phase, the symmetry of the embryo changes from radial to bilateral, giving rise to a hypocotyl with a shoot meristem surrounded by the two cotyledonary primordia at the apical pole and a root meristem at the basal pole. In the late phase, during maturation the embryo achieves its maximum size and the seed accumulates storage proteins and lipids. Maturation is ended by the desiccation stage in which the seed water content decreases rapidly and the embryo passes into metabolic quiescent state. Dormancy ends with seed germination, and development continues from the shoot and the root meristem regions.

The precise regulatory mechanisms that control cell and organ differentiation during the initial phase of embryogenesis are largely unknown. The plant hormone abscisic acid (ABA) is thought to play a role during late embryogenesis, mainly in the maturation stage by inhibiting germination during embryogenesis (Black, M. (1991). In Abscisic Acid: Physiology and Biochemistry, W. J. Davies and H. G. Jones, eds. (Oxford: Bios Scientific Publishers Ltd.), pp. 99–124); and Koornneef, M., and Karssen, C. M. (1994). In Arabidopsis, E. M. Meyerowitz and C. R. Sommerville, eds. (Cold Spring Harbor: Cold Spring Harbor Laboratory Press), pp. 313–334). Mutations that effect seed development and are ABA insensitive have been identified in Arabidopsis and maize. The ABA insensitive (abi3) mutant of Arabidopsis and the viviparous1 (vp1) mutant of maize are detected mainly during late embryogenesis (McCarty, et al. (1989) *Plant Cell* 1:523–532 and Parcy et al. (1994) *Plant Cell* 6:1567–1582). Both the VP1 gene and the ABI3 genes have been isolated and were found to share conserved regions (Giraudat, J. (1995) *Current Opinion in Cell Biology* 7:232–238 and McCarty, D. R. (1995). *Annu. Rev. Plant Physiol. Plant Mol. Biol.* 46:71–93). The VP1 gene product has been shown to function as a transcription activator (McCarty, et al. (1991) *Cell* 66:895–906). It has been suggested that ABI3 has a similar function.

In spite of the recent progress in defining the genetic control of embryo development, further progress is required in the identification and analysis of genes expressed specifically in the embryo and seed. Characterization of such genes would allow for the genetic engineering plants with a variety of desirable traits. For instance, modulation of the expression of genes that control embryo development may be used to alter traits such as accumulation of storage proteins in leaves and cotyledons. Alternatively, promoters from embryo or seed-specific genes can be used to direct expression of desirable heterologous genes to the embryo or seed. The present invention addresses these and other needs.

SUMMARY OF THE INVENTION

Figure 1:
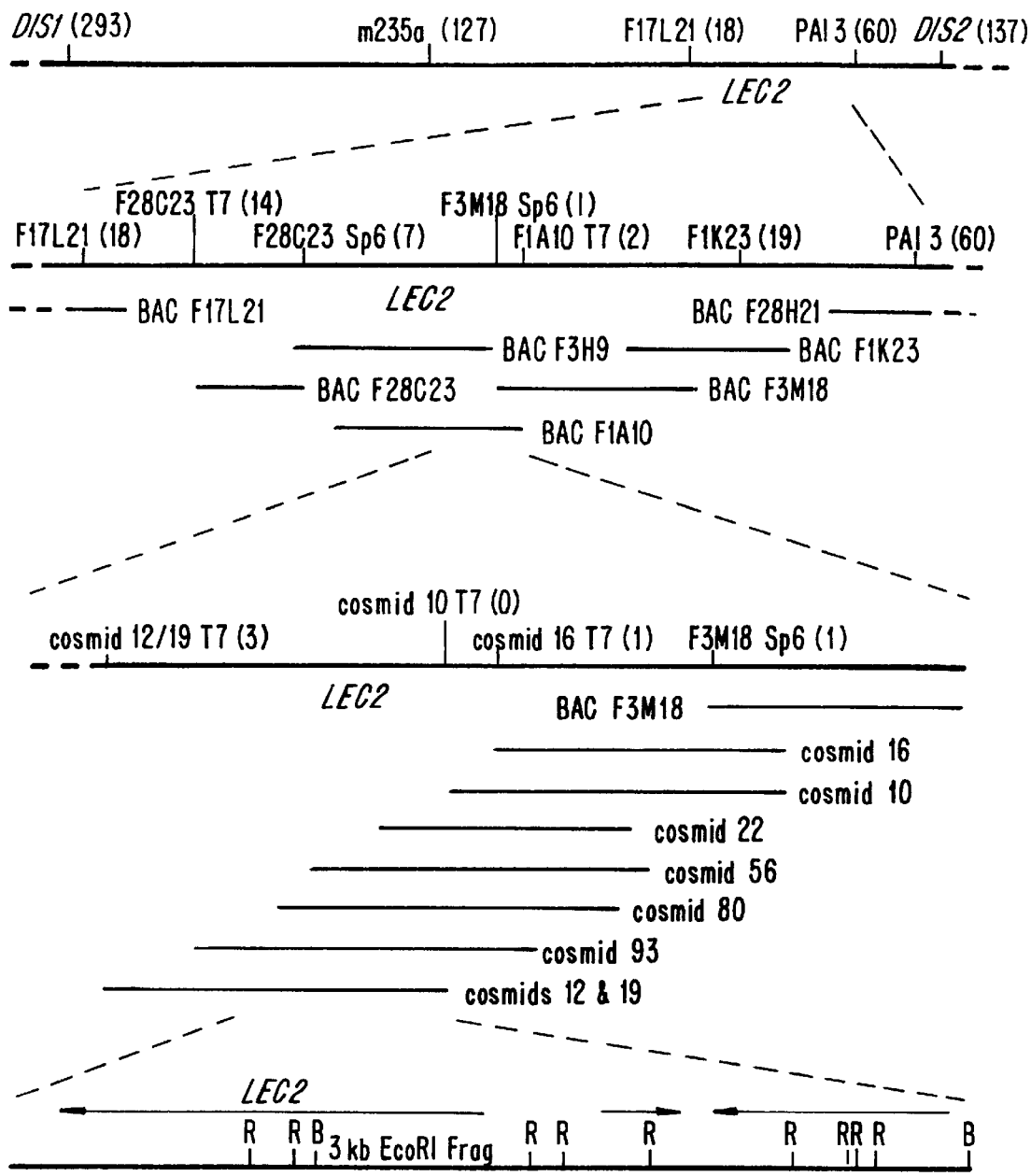
FIG. 1 is a schematic representation showing the details of the mapping strategy of LEC2.

This invention provides an isolated nucleic acid comprising a polynucleotide sequence, or complement thereof, encoding a LEC2 polypeptide exhibiting at least 65% sequence identity to SEQ ID NO:2. In some embodiments, the nucleic acid does not include bacterial artificial chromosome F3H9 (Genbank accession number AC021044). For instance, the sequence can be SEQ ID NO:1. In some embodiments, the polypeptide is SEQ ID NO:2.

The nucleic acid can further comprise a promoter operably linked to the polynucleotide. In some embodiments, the promoter is a constitutive. The promoter can be a LEC2 promoter, i.e. from a LEC2 gene. For example, in some embodiments, the LEC2 promoter can be at least 70% identical to SEQ ID NO:3. Thus, the promoter can comprise SEQ ID NO:3. The promoter can further comprise a sequence at least 70% identical to SEQ ID NO:4. For instance, the promoter can further comprise SEQ ID NO:4. In some embodiments, the polynucleotide sequence is linked to the promoter in an antisense orientation.

The invention also provides for an isolated nucleic acid comprising a polynucleotide sequence exhibiting at least 65% sequence identity to SEQ ID NO:1. In some embodiments, the nucleic acid does not include bacterial artificial chromosome F3H9 (Genbank accession number AC021044).

The invention also provides for an expression cassette comprising a promoter operably linked to a heterologous polynucleotide sequence, or complement thereof, encoding a LEC2 polypeptide with at least 65% sequence identity to SEQ ID NO:2. In some embodiments, the encoded LEC2 polypeptide is SEQ ID NO:2. In some embodiments, the polynucleotide sequence is SEQ ID NO:1. The promoter of the expression cassette can be constitutive and/or can be from the LEC2 gene. For example, in one embodiment, the promoter comprises a polynucleotide at least 70% identical to SEQ ID NO:3. The promoter can be SEQ ID NO:3. In some embodiments, the promoter can further comprise a polynucleotide at least 70% identical to SEQ ID NO:4. The promoter can further comprise SEQ ID NO:4. In some embodiments, the polynucleotide is linked to the promoter in an antisense orientation.

The present invention also provides for an expression cassette for the expression of a heterologous polynucleotide in a plant cell. This expression cassette comprises a promoter at least 70% identical to SEQ ID NO:3 operably linked to a heterologous polynucleotide. In some embodiments, the promoter comprises SEQ ID NO:3. In some embodiments, the promoter further comprises a polynucleotide at least 70% identical to SEQ ID NO:4. The promoter can further comprise SEQ ID NO:4.

The invention also provides for a host cell comprising an exogenous polynucleotide sequence, or complement thereof, encoding a LEC2 polypeptide exhibiting at least 65% sequence identity to SEQ ID NO:2. In some embodiments, the nucleic acid does not include bacterial artificial chromosome F3H9 (Genbank accession number AC021044). In some embodiments, the host cell is not an Arabidopsis cell. The nucleic acid can further comprise a promoter operably linked to the polynucleotide. In some embodiments, the promoter is a constitutive. The promoter can be a LEC2 promoter, i.e. from a LEC2 gene. For example, in some embodiments, the LEC2 promoter can be at least 70% identical to SEQ ID NO:3. Thus, the promoter can comprise SEQ ID NO:3. The promoter can further comprise a sequence at least 70% identical to SEQ ID NO:4. For instance, the promoter can further comprise SEQ ID NO:4. In some embodiments, the host cell is selected from the group comprising a plant, bacterial, yeast, fungal and animal cell.

The invention also provides for an isolated polypeptide comprising an amino acid sequence at least 65% identical to SEQ ID NO:2 and which is capable of exhibiting at least one of the biological activities of the polypeptide displayed in SEQ ID NO:2 or a fragment thereof. The invention also provides for an antibody that binds to such a polypeptide.

The invention provides for a method of introducing an isolated nucleic acid into a host cell comprising providing an isolated nucleic acid comprising a polynucleotide sequence, or complement thereof, encoding a LEC2 polypeptide exhibiting at least 65% sequence identity to SEQ ID NO:2, and contacting the nucleic acid with the host cell under conditions that permit insertion of the nucleic acid into the host.

The invention also provides for a method of modulating transcription comprising introducing into a host cell an expression cassette comprising a promoter operably linked to a heterologous LEC2 polynucleotide which encodes a LEC2 polypeptide at least 65% identical to SEQ ID NO:2 and detecting a host cell with modulated transcription. In some embodiments, the polynucleotide encodes SEQ ID NO:2. For instance, the polynucleotide can be SEQ ID NO:1.

In some embodiments, the host cell is a plant cell. In some embodiments, the host cell is not an Arabidopsis cell. In some embodiments, the expression cassette is introduced by Agrobacterium. In another embodiment, the expression cassette is introduced by a sexual cross. In some embodiments, the modulation of transcription results in the induction of embryonic characteristics in a plant. In some embodiments, modulation of transcription results in the induction of seed development. In some embodiments, a plant is regenerated from the plant cell.

The invention also provides a method of detecting a nucleic acid in a sample comprising (1) providing an isolated nucleic acid molecule comprising a polynucleotide sequence, or complement thereof, encoding a LEC2 polypeptide exhibiting at least 65% sequence identity to SEQ ID NO:2, (2) contacting the isolated nucleic acid molecule with a sample under conditions which permit a comparison of the sequence of the isolated nucleic acid molecule with the sequence of DNA in the sample, and (3) analyzing the result of the comparison. In some embodiments, the isolated nucleic acid molecule and the sample are contacted under conditions which permit the formation of a duplex between complementary nucleic acid sequences.

The invention also provides a transgenic plant or transgenic plant cell comprising an exogenous polynucleotide sequence, or complement thereof, encoding a LEC2 polypeptide exhibiting at least 65% sequence identity to SEQ ID NO:2. In some embodiments, a plant is regenerated from a plant cell. The sequence can be SEQ ID NO:1. In some embodiments, the polypeptide is SEQ ID NO:2.

The nucleic acid can further comprise a promoter operably linked to the polynucleotide. In some embodiments, the promoter is a constitutive. The promoter can be a LEC2 promoter, i.e. from a LEC2 gene. For example, in some embodiments, the LEC2 promoter can be at least 70% identical to SEQ ID NO:3. Thus, the promoter can comprise SEQ ID NO:3. The promoter can further comprise a sequence at least 70% identical to SEQ ID NO:4. For instance, the promoter can further comprise SEQ ID NO:4. In some embodiments, the polynucleotide sequence is linked to the promoter in an antisense orientation.

Definitions

The phrase "nucleic acid" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "polynucleotide sequence" or "nucleic acid sequence" includes both the sense and antisense strands of a nucleic acid as either individual single strands or in the duplex. It includes, but is not limited to, self-replicating plasmids, chromosomal sequences, and infectious polymers of DNA or RNA.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The phrase "host cell" refers to a cell from any organism. Preferred host cells are derived from plants, bacteria, yeast, fungi, insects or other animals. Methods for introducing polynucleotide sequences into various types of host cells are well known in the art.

The "biological activity of a polypeptide" refers to any molecular activity or phenotype that is caused by the polypeptide. For example, the ability to transfer a phosphate to a substrate or the ability to bind a specific DNA sequence is a biological activity. One biological activity of LEC2 is the ability to induce embryonic characteristics on plant organs.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant, or a predecessor generation of the plant, by any means other than by a sexual cross. Examples of means by which this can be accomplished are described below, and include Agrobacterium-mediated transformation, biolistic methods, electroporation, in planta techniques, and the like.

As used herein an "embryo-specific gene" or "seed specific gene" is a gene that is preferentially expressed during embryo development in a plant. For purposes of this disclosure, embryo development begins with the first cell divisions in the zygote and continues through the late phase of embryo development (characterized by maturation, desiccation, dormancy), and ends with the production of a mature and desiccated seed. Embryo-specific genes can be further classified as "early phase-specific" and "late phase-specific". Early phase-specific genes are those expressed in embryos up to the end of embryo morphogenesis. Late phase-specific genes are those expressed from maturation through to production of a mature and desiccated seed.

A "LEC2 polynucleotide" is a nucleic acid sequence comprising (or consisting of) a coding region of about 50 to about 6800 nucleotides, sometimes from about 100 to about 3000 nucleotides and sometimes from about 300 to about 1300 nucleotides, which hybridizes to SEQ ID NO:1 under stringent conditions (as defined below), or which encodes a LEC2 polypeptide or fragment of at least 15 amino acids thereof. LEC2 polynucleotides can also be identified by their ability to hybridize under low stringency conditions (e.g., Tm ~40° C.) to nucleic acid probes having a the sequence of SEQ ID NO:1. SEQ ID NO:1, SEQ ID NO:5 (the LEC2 cDNA) and SEQ ID NO:6 are examples of LEC2 polynucleotides.

A "promoter from a LEC2 gene" or "LEC2 promoter" will typically be about 500 to about 4000 nucleotides in length, usually from about 720 to 3200. Exemplary promoter sequences are shown as SEQ ID NO:3 and SEQ ID NO:4. SEQ ID NO:3 represents the 5' untranslated region of the LEC2 and SEQ ID NO:4 represents the 3' untranslated region of LEC2. A LEC2 promoter can also be identified by its ability to direct expression in early stage seeds as well as during early and mid-stage embryogenesis. The promoter does not provide significant expression in leaf tissue.

A "LEC2 polypeptide" is a sequence of about 50 to about 400, sometimes 100 to 150, and preferably 363 amino acid residues encoded by a LEC2 polynucleotide. LEC2 polypeptides are characterized by the presence of a B3 domain. For instance amino acid residues 165 to 277 represent the B3 domain of the polypeptide shown in SEQ ID NO:2. The B3 domain is known in the art and is shared by other transcription factors including VIVIPAROUS1 (VP1) ((McCarty, et al. (1989) *Plant Cell* 1:523–532), AUXIN RESPONSE FACTOR 1 (ARF1) (Ulmasov, T. et al. (1997) *Science* 276:1865–1868), FUSCA3 (Luerben, H., et al. (1998) *Plant J.* 15:755–764) and ABI3 (Giraudat, J., et al. (1992) *Plant Cell* 4, 1251–1261). The B3 domains of VPI (Suzuki, M. et al. (1997) *Plant Cell* 9:799–807) and ARF1 (Ulmasov, T., et al., supra) have been shown to be DNA binding domains. The B3 domain of LEC2 is therefore also a DNA binding domain.

As used herein, a homolog of a particular embryo-specific gene (e.g., SEQ ID NO:1) is a second gene in the same plant type or in a different plant type, which has a polynucleotide sequence of at least 50 contiguous nucleotides which are substantially identical (determined as described below) to a sequence in the first gene. It is believed that, in general, homologs share a common evolutionary past.

"Increased or enhanced LEC2 activity or expression of the LEC2 gene" refers to an augmented change in LEC2 activity. Examples of such increased activity or expression include the following. LEC2 activity or expression of the LEC2 gene is increased above the level of that in wild-type, non-transgenic control plants (i.e. the quantity of LEC2 activity or expression of the LEC2 gene is increased). LEC2 activity or expression of the LEC2 gene is in an organ, tissue or cell where it is not normally detected in wild-type, non-transgenic control plants (i.e. spatial distribution of LEC2 activity or expression of the LEC2 gene is increased). LEC2 activity or expression is increased when LEC2 activity or expression of the LEC2 gene is present in an organ, tissue or cell for a longer period than in a wild-type, non-transgenic controls (i.e. duration of LEC2 activity or expression of the LEC2 gene is increased).

A "polynucleotide sequence from" a particular gene is a subsequence or full length polynucleotide sequence of an embryo-specific gene which, when present in a transgenic plant, has the desired effect. For example, one effect is inhibition of expression of the endogenous gene driving expression of an heterologous polynucleotide. A full length sequence of a particular gene disclosed here may contain about 95%, usually at least about 98% of an entire sequence shown in the Sequence Listing, below.

The term "reproductive tissues" as used herein includes fruit, ovules, seeds, pollen, pistols, flowers, or any embryonic tissue.

An "expression cassette" refers to a nucleic acid construct, which when introduced into a host cell, results in transcription and/or translation of a RNA or polypeptide, respectively. Antisense or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the term "polynucleotide sequence from" a particular embryo-specific gene, such as LEC2. In addition, the term specifically includes sequences (e.g., full length sequences) substantially identical (determined as described below) with a LEC2 gene sequence and that encode proteins that retain the function of a LEC2 polypeptide.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least:25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters, as described below. Accordingly, LEC2 sequences of the invention include nucleic acid sequences that have substantial identity to SEQ ID NO:1, SEQ ID NO:3 and SEQ ID NO:4. LEC2 sequences of the invention also include polypeptide sequences having substantial identify to SEQ ID NO:2. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 90%, 95%, or 99%. Most preferred embodiments include 61%, 62%, 63%, 64%, 65%, 66%, 67%, 68%, 69%, 70%, 71%, 72%, 73%, 74% and 75%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

In the present invention, mRNA encoded by embryo-specific genes of the invention can be identified in Northern blots under stringent conditions using cDNAs of the invention or fragments of at least about 100 nucleotides. For the purposes of this disclosure, stringent conditions for such RNA-DNA hybridizations are those which include at least one wash in 0.2×SSC at 63° C. for 20 minutes, or equivalent conditions. Genomic DNA or cDNA comprising genes of the invention can be identified using the same cDNAs (or fragments of at least about 100 nucleotides) under stringent conditions, which for purposes of this disclosure, include at least one wash (usually 2) in 0.2×SSC at a temperature of at least about 50° C., usually about 55° C., for 20 minutes, or equivalent conditions.

Detailed Description

The present invention provides new polypeptides useful for genetically engineering plants. In particular, the invention provides a new gene from Arabidopsis referred to here as LEC2. Modulation of the expression of this gene can be used to manipulate a number of useful traits, such as inducing seed development. Polynucleotide sequences from the genes of the invention can also be used, for instance, to direct expression of desired heterologous genes in embryos (in the case of promoter sequences) or to modulate development of embryos or embyonic characteristics on other organs (e.g., by enhancing or decreasing expression of the gene in a transgenic plant).

In yet another use, nucleic acids of the invention can be used in the development of apomictic plant lines (i.e., plants in which asexual reproductive processes occur in the ovule, see, Koltunow, A. *Plant Cell* 5:1425–1437 (1993) for a discussion of apomixis). Apomixis provides a novel means to select and fix complex heterozygous genotypes that cannot be easily maintained by traditional breeding. Thus, for instance, new hybrid lines with desired traits (e.g., hybrid vigor) can be obtained and readily maintained. The LEC2 nucleic acids of the invention can also be used in combination with other genes in the production of apomictic plant lines.

Generally, the nomenclature and the laboratory procedures in recombinant DNA technology described below are those well known and commonly employed in the art.

Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., Molecular Cloning—A Laboratory Manual, 2nd. ed., Cold Spring Harbor Laboratory, Cold Spring Harbor, N.Y., (1989).

Isolation of nucleic acids of the invention

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying embryo-specific genes from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990). Appropriate primers for amplification of the genomic region of LEC2 include the following three primer pairs: D2F-5'TTTCAGAATACGCAAAAACGAC3' (SEQ ID NO:7) and D2R-5'AACTATCCTCCCGAGTGACC3' (SEQ ID NO:8); Ef-5' AGATGGCAAGGATCAACAGG3'(SEQ ID NO:9) and BlastR-5'CTTGCTTTCGTCCTCGTATATTG3' (SEQ ID NO:10); and F2F-5'TTTGTGAAGCAAAATGGAGC3' (SEQ ID NO:11) and Stop-5' CGGATGAACCCACGTACG3'(SEQ ID NO:12). Appropriate primers for amplification of the LEC2 cDNA include the following pair: 5'AAATGGATAACTTCTTACCCTTTCC3'(SEQ ID NO:13) and 5'CGGATGAACCCACGTACG3' (SEQ ID NO:14). The amplification conditions are typically as follows. Reaction components: 10 mM Tris-HCl, pH 8.3, 50 mM potassium chloride, 1.5 mM magnesium chloride, 0.001% gelatin, 200 µM dATP, 200 µM dCTP, 200 µM dGTP, 200 µM dTTP, 0.4 µM primers, and 100 units per ml Taq polymerase. Program: 96 C for 3 min., 30 cycles of 96 C for 45 sec., 50 C for 60 sec., 72 C for 60 sec, followed by 72 C for 5 min.

Polynucleotides may also be synthesized by well-known techniques as described in the technical literature. See, e.g., Carruthers et al., Cold Spring Harbor Symp. *Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

The genus of LEC2 nucleic acid sequences of the invention includes genes and gene products identified and characterized by analysis using the sequences nucleic acid sequences, including SEQ ID NO:1 and protein sequences, including SEQ ID NO:2. LEC2 sequences of the invention include nucleic acid sequences having substantial identity to SEQ ID NO:1. LEC2 sequences of the invention include polypeptide sequences having substantial identify to SEQ ID NO:2.

Use of nucleic acids of the invention

Genetic and molecular analysis of genes involved in embryo development revals a number of of plant qualities that can be modulated using LEC2 nucleic acids of the invention. The Arabidopsis LEAFY COTYLEDON (LEC) genes, LEC1, LEC2, and FUSCA3 (FUS3), control several aspects of embryo and seed development (Baumlein, H., et al. (1994) *Plant J.* 6:379–387; Keith, K., et al. (1994) *Plant Cell* 6:589–600; Lotan, T., et al. (1998) *Cell* 93:1195–1205; Luerben, H., et al. (1998) *Plant J.* 15:755–764; Meinke, D. W. (1992) *Science* 258:1647–1650; Meinke, D. W., et al. (1994) *Plant Cell* 6:1049–1064; Parcy, F., et al. (1997) *Plant Cell* 9:1265–1277; West, M. A. L., et al. (1994) *Plant Cell* 6:1731–1745). Analyses of plants with mutations in these genes suggest that they are required for the maintenance of suspensor cell fate early in embryogenesis, the specification of cotyledon identity, the induction and/or maintenance of the late maturation phase, and the suppression of postgerminative development during seed development (Harada, J. J. (1997) In Advances in Cellular and Molecular Biology if Plants, Volume 4, Cellular and Molecular Biology of Seed Development, B. A. Larkins and I. K. Vasi, eds. (Dordrecht: Kluwer Academic Publishers), pp. 545–592). For example, abnormal cell divisions occur in the suspensors of lec2 mutants indicating defects early in embryogenesis (Lotan et al., supra). Unlike wild type embryos, lec2 mutants have trichomes on their cotyledons (Meinke et al. (1994), supra). Because trichomes are a leaf-trait in Arabidopsis, the mutants have incompletely specified cotyledons that have reverted partially to leaves. Although lec2 mutant embryos can survive silique drying (Meinke et al. (1994), supra), parts of the cotyledons are intolerant of desiccation. These same regions of the cotyledons are also abnormal in that they do not accumulate RNAs normally expressed during late embryogenesis. Furthermore, lec2 mutant embryos have activated shoot apical meristems that are normally characteristic of seedlings, indicating that postgerminative development has occurred prematurely. These latter observations suggest that the lec2 mutation causes defects in the late seed maturation phase of embryo development. Because the LEC genes play regulatory roles in many aspects of seed development, they are central regulators of embryogenesis.

The requirement for the LEC genes for many different aspects of embryogenesis suggest that they operate to control and coordinate seed development (Lotan et al., supra). Studies with the LEC1 gene suggest that these genes may play a fundamental role in initiating seed development by establishing an environment that permits embryogenesis to occur. LEC1 RNA is detected in the zygote but not in prefertilization ovules, suggesting that the gene functions at the earliest stages of embryo development. The LEC1 gene is normally expressed only during seed development. Experiments in which the LEC1 gene was engineered to be expressed postembryonically resulted in the induction of ectopic embryo formation from vegetative cells (Lotan et al., supra). Together, these results suggest that LEC1 is sufficient to establish a cellular environment that permits embryo formation to occur.

Several lines of reasoning suggest that LEC2 and FUS3 may function similarly with LEC1. First, LEC1 is sufficient but not necessary to induce embryo formation. That is, lec1 mutants still make embryos suggesting that other genes may have overlapping functions with LEC1 (Lotan et al., supra). Second, genetic studies show that LEC2 interacts synergistically with LEC1 suggesting that these genes interact physically or have partially redundant functions (Lotan et al., supra; Meinke et al. (1994), supra). LEC2 and FUS3 also interact synergistically. The most simple interpretation of these results is that LEC1, LEC2, and FUS3 play fundamental roles in the initiation of embryo formation.

The identities of the LEC genes are consistent with their roles as regulatory genes. LEC1 encodes a homolog of the HAP3 subunit of the CCAAT box binding transcription factor (Lotan et al., supra). The FUS3 protein contains the B3 domain of the ABA INSENSTIVE3/Viviparous1 transcription factor (Giraudat, J., et al. (1992) *Plant Cell* 4, 1251–1261; Luessen et al., supra; McCarty, D. R., et al. (1991) *Cell* 66, 895–906). This B3 domain contains a DNA binding domain (Suzuki, M., et al. (1997) *Plant Cell* 9, 799–807).

Use of nucleic acids of the invention to inhibit gene expression

The isolated sequences prepared as described herein, can be used to prepare expression cassettes useful in a number of techniques. For example, expression cassettes of the invention can be used to suppress endogenous LEC2 gene expression. Inhibiting expression can be useful, for instance, in weed control (by transferring an inhibitory sequence to a weedy species and allowing it to be transmitted through sexual crosses) or to produce fruit with small and non-viable seed.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The antisense nucleic acid sequence transformed into plants will be substantially identical to at least a portion of the endogenous embryo-specific gene or genes to be repressed. The sequence, however, does not have to be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most vairance between family members.

Another means of inhibiting LEC2 function in a plant is by creation of dominant negative mutations. In this approach, non-functional, mutant LEC2 polypeptides, which retain the ability to interact with wild-type subunits are introduced into a plant.

Use of Nucleic Acids of the Invention to Enhance Gene Expression

Isolated sequences prepared as described herein can also be used to prepare expression cassettes that enhance or increase endogenous LEC2 gene expression. Where overexpression of a gene is desired, the desired gene from a different species may be used to decrease potential sense suppression effects. Enhanced expression of LEC2 polynucleotides is useful, for example, to increase storage protein content in plant tissues. Such techniques may be particularly useful for improving the nutritional value of plant tissues.

Any of a number of means well known in the art can be used to increase LEC2 activity in plants. Enhanced expression is useful, for example, to induce embyonic characteristics in plants or plant organs. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, one or several LEC2 genes can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed. As explained above, LEC2 polypeptides are related to the FUSCA3 gene product, which is a transcription factor. Thus, without being bound to any particular theory or mechanism, LEC2 is likely to act as a transcriptional modulator.

The DNA binding activity, and, therefore, transcription activation function, of LEC2 polypeptides is thought to be modulated by an amino acid motif known as the B3 domain, as described above. For instance, amino acid positions 165 to 277 represent the B3 domain of SEQ ID NO:2. Thus, the polypeptides of the invention will often retain these sequences.

Modification of endogenous LEC2 genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorski, et al., (1991). Meth. Enzymol. 194: 302–318). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications by specifically targeting the LEC2 gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an LEC2 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered LEC2 gene expression in transgenic plants. The mutated gene will interact with the target wild-type gene in such a way that homologous recombination and targeted replacement of the wild-type gene will occur in transgenic plant cells, resulting in suppression of LEC2 activity.

Alternatively, oligonucleotides composed of a contiguous stretch of RNA and DNA residues in a duplex conformation with double hairpin caps on the ends can be used. The RNA/DNA sequence is designed to align with the sequence of the target LEC2 gene and to contain the desired nucleotide change. Introduction of the chimeric oligonucleotide on an extrachromosomal T-DNA plasmid results in efficient and specific LEC2 gene conversion directed by chimeric molecules in a small number of transformed plant cells. This method is described in Cole-Strauss et al., *Science* 273:1386–1389 (1996) and Yoon et al., *Proc. Natl. Acad. Sci. USA* 93: 2071–2076 (1996).

In other embodiments, the promoters derived from the LEC2 genes of the invention can be used to drive expression of heterologous genes in an embryo-specific or seed-specific manner, such that desired gene products are present in the embryo, seed, or fruit. Suitable structural genes that could be used for this purpose include genes encoding proteins useful in increasing the nutritional value of seed or fruit. Examples include genes encoding enzymes involved in the biosynthesis of antioxidants such as vitamin A, vitamin C, vitamin E and melatonin. Other suitable genes encoding proteins involved in modification of fatty acids, or in the biosynthesis of lipids, proteins, and carbohydrates. Still other genes can be those encoding proteins involved in auxin and auxin analog biosynthesis for increasing fruit size, genes encoding pharmaceutically useful compounds, and genes encoding plant resistance products to combat fungal or other infections of the seed.

Typically, desired promoters are identified by analyzing the 5' sequences of a genomic clone corresponding to the embryo-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions −80 to −100, there is typically a promoter element with a series of adenines surrounding the trinucleotide G (or T) N G. J. Messing et al., in Genetic Engineering in Plants, pp.221–227 (Kosage, Meredith and Hollaender, eds. (1983)).

A number of methods are known to those of skill in the art for identifying and characterizing promoter regions in plant genomic DNA (see, e.g., Jordano, et al., *Plant Cell*, 1: 855–866 (1989); Bustos, et al., *Plant Cell*, 1:839–854 (1989); Green, et al., *EMBO J.* 7, 4035–4044 (1988); Meier, et al., *Plant Cell*, 3, 309–316 (1991); and Zhang, et al., *Plant Physiology* 110: 1069–1079 (1996)).

Preparation of recombinant vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens,* and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the LEC2 genes described here are particularly useful for directing gene expression so that a desired gene product is located in embryos or seeds. Other suitable promoters include those from genes encoding storage proteins or the lipid body membrane protein, oleosin. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

LEC2 nucleic acid sequences of the invention are expressed recombinantly in plant cells to enhance and increase levels of endogenous LEC2 polypeptides. Alternatively, antisense or other LEC2 constructs (described above) are used to suppress LEC2 levels of expression. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421–477 (1988). A DNA sequence coding for a LEC2 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides a LEC2 nucleic acid operably linked to a promoter which, in a preferred embodiment, is capable of driving the transcription of the LEC2 coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. Typically, as discussed above, desired promoters are identified by analyzing the 5' sequences of a genomic clone corresponding to the embryo-specific genes described here.

Constitutive Promoters

A promoter fragment can be employed which will direct expression of LEC2 nucleic acid in all transformed cells or tissues, e.g. as those of a regenerated plant. Such promoters are referred to herein as "constitutive" promoters and are active under most environmental conditions and states of development or cell differentiation. Promoters that drive expression continuously under physiological conditions are referred to as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless (1997) *Arch. Virol.* 142:183–191); the 1'- or 2'-promoter derived from T-DNA of *Agrobacterium tumafaciens* (see, e.g., Mengiste (1997) supra; O'Grady (1995) *Plant Mol. Biol.* 29:99–108); the promoter of the tobacco mosaic virus; the promoter of Figwort mosaic virus (see, e.g., Maiti (1997) *Transgenic Res.* 6:143–156); actin promoters, such as the Arabidopsis actin gene promoter (see, e.g., Huang (1997) *Plant Mol. Biol.* 1997 33:125–139); alcohol dehydrogenase (Adh) gene promoters (see, e.g., Millar (1996) *Plant Mol. Biol.* 31:897–904); ACT11 from Arabidopsis (Huang et al. *Plant Mol. Biol.* 33:125–139 (1996)), Cat3 from Arabidopsis (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), Gpc2 from maize (GenBank No. U45855, Manjunath et al., *Plant Mol. Biol.* 33:97–112 (1997)), other transcription initiation regions from various plant genes known to those of skill. See also Holtorf (1995) "Comparison of different constitutive and inducible promoters for the overexpression of transgenes in *Arabidopsis thaliana,*" *Plant Mol. Biol.* 29:637–646.

Inducible Promoters

Alternatively, a plant promoter may direct expression of the LEC2 nucleic acid of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897–909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (Glycine max L.) (Liu (1997) *Plant Physiol.* 115:397–407); the auxin-responsive Arabidopsis GST6 promoter (also responsive to salicylic acid and hydrogen peroxide) (Chen (1996) *Plant J.* 10: 955–966); the auxin-inducible parC promoter from tobacco (Sakai (1996) 37:906–913); a plant biotin response element (Streit (1997) *Mol. Plant Microbe Interact.* 10:933–937); and, the promoter responsive to the stress hormone abscisic acid (Sheen (1996) *Science* 274:1900–1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568–577); application of different herbicide safeners induces distinct gene expression patterns, including expression in the root, hydathodes, and the shoot apical meristem. LEC2 coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465–473); or, a salicylic acid-responsive element (Stange (1997) *Plant J.* 11:1315–1324.

Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the LEC2 genes of the invention are particularly useful for tissue-specific direction of gene expression so that a desired gene product is generated only or preferentially in embryos or seeds, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

Suitable seed-specific promoters are derived from the following genes: MAC1 from maize (Sheridan (1996) *Genetics* 142:1009–1020); Cat3 from maize (GenBank No. L05934, Abler (1993) *Plant Mol. Biol.* 22:10131–1038); vivparous-1 from Arabidopsis (Genbank No. U93215); atmyc1 from Arabidopsis (Urao (1996) *Plant Mol. Biol.* 32:571–57; Conceicao (1994) *Plant* 5:493–505); napA from *Brassica napus* (GenBank No. J02798, Josefsson (1987) JBL 26:12196–1301); and the napin gene family from *Brassica napus* (Sjodahl (1995) *Planta* 197:264–271).

The ovule-specific BEL1 gene described in Reiser (1995) *Cell* 83:735–742, GenBank No. U39944, can also be used. See also Ray (1994) *Proc. Natl. Acad. Sci. USA* 91:5761–5765. The egg and central cell specific FIE1 promoter is also a useful reproductive tissue-specific promoter.

Sepal and petal specific promoters are also used to express LEC2 nucleic acids in a reproductive tissue-specific manner. For example, the Arabidopsis floral homeotic gene APETALA1 (AP1) encodes a putative transcription factor that is expressed in young flower primordia, and later becomes localized to sepals and petals (see, e.g., Gustafson-Brown (1994) *Cell* 76:131–143; Mandel (1992) *Nature* 360:273–277). A related promoter, for AP2, a floral homeotic gene that is necessary for the normal development of sepals and petals in floral whorls, is also useful (see, e.g., Drews (1991) *Cell* 65:991–1002; Bowman (1991) *Plant Cell* 3:749–758). Another useful promoter is that controlling the expression of the unusual floral organs (ufo) gene of Arabidopsis, whose expression is restricted to the junction between sepal and petal primordia (Bossinger (1996) *Development* 122:1093–1102).

A maize pollen-specific promoter has been identified in maize (Guerrero (1990) *Mol. Gen. Genet.* 224:161–168). Other genes specifically expressed in pollen are described, e.g., by Wakeley (1998) *Plant Mol. Biol.* 37:187–192; Ficker (1998) *Mol. Gen. Genet.* 257:132–142; Kulikauskas (1997) *Plant Mol. Biol.* 34:809–814; Treacy (1997) *Plant Mol. Biol.* 34:603–611.

Other suitable promoters include those from genes encoding embryonic storage proteins. For example, the gene encoding the 2S storage protein from *Brassica napus*, Dasgupta (1993) *Gene* 133:301–302; the 2s seed storage protein gene family from Arabidopsis; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from Arabidopsis, Genbank No. Z17657; the gene encoding oleosin 18 kD from maize, GenBank No. J05212, Lee (1994) *Plant Mol. Biol.* 26:1981–1987; and, the gene encoding low molecular weight sulphur rich protein from soybean, Choi (1995) *Mol Gen, Genet.* 246:266–268, can be used. The tissue specific E8 promoter from tomato is particularly useful for directing gene expression so that a desired gene product is located in fruits.

A tomato promoter active during fruit ripening, senescence and abscission of leaves and, to a lesser extent, of flowers can be used (Blume (1997) *Plant J.* 12:731–746). Other exemplary promoters include the pistol specific promoter in the potato (*Solanum tuberosum* L.) SK2 gene, encoding a pistil-specific basic endochitinase (Ficker (1997) *Plant Mol. Biol* 35:425–431); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the LEC2 nucleic acids of the invention. For example, promoters controlling patatin, the major storage protein of the potato tuber, can be used, see, e.g., Kim (1994) *Plant Mol. Biol.* 26:603–615; Martin (1997) *Plant J.* 11:53–62. The ORF13 promoter from Agrobacterium rhizogenes which exhibits high activity in roots can also be used (Hansen (1997) *Mol Gen. Genet.* 254:337–343. Other useful vegetative tissue-specific promoters include: the tarin promoter of the gene encoding a globulin from a major taro (Colocasia esculenta L. Schott) corm protein family, tarin (Bezerra (1995) *Plant Mol. Biol.* 28:137–144); the curculin promoter active during taro corm development (de Castro (1992) *Plant Cell* 4:1549–1559) and the promoter for the tobacco root-specific gene TobRB7, whose expression is localized to root meristem and immature central cylinder regions (Yamamoto (1991) *Plant Cell* 3:371–382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91–95). A ribulose bisphosphate carboxylase promoters expressed almost exclusively in mesophyll cells in leaf blades and leaf sheaths at high levels, described by Matsuoka (1994) *Plant J.* 6:311–319, can be used. Another leaf-specific promoter is the light harvesting chlorophyll a/b binding protein gene promoter, see, e.g., Shiina (1997) *Plant Physiol.* 115:477–483; Casal (1998) *Plant Physiol.* 116:1533–1538. The *Arabidopsis thaliana* myb-related gene promoter (Atmyb5) described by Li (1996) *FEBS Lett.* 379:117–121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285–1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423–433; and, Long (1996) *Nature* 379:66–69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517–527). Also useful are kn1-related genes from maize and other species which show meristem-specific expression, see, e.g., Granger (1996) *Plant Mol Biol.* 31:373–378; Kerstetter (1994) *Plant Cell* 6:1877–1887; Hake (1995) *Philos. Trans. R. Soc. Lond. B. Biol. Sci.* 350:45–51. For example, the Arabidopsis thaliana KNAT1 promoter. In the shoot apex, KNAT1 transcript is localized primarily to the shoot apical meristem; the expression of KNAT1 in the shoot meristem decreases during the floral transition and is restricted to the cortex of the inflorescence stem (see, e.g., Lincoln (1994) *Plant Cell* 6:1859–1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a LEC2 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679–1683; the rice tungro baciliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129–1139).

Production of transgenic plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional Agrobacterium tumefaciens host vector. The virulence functions of the Agrobacterium tumefaciens host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *Embo J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Agrobacterium tumefaciens-mediated transformation techniques, including disarming and use of binary vectors, are well described in the scientific literature. See, for example Horsch et al. *Science* 233:496–498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124–176, MacMillilan Publishing Company, New York, 1983; and Binding, Regeneration of Plants, Plant Protoplasts, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any plant. Thus, the invention has use over a broad range of plants, including species from the genera Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna, and, Zea. The LEC2 genes of the invention are particularly useful in the production of transgenic plants in the genus Brassica. Examples include broccoli, cauliflower, brussel sprouts, canola, and the like.

Use and Recombinant Expression of LEC2 in Combination with Other Genes

The LEC2 nucleic acids of the invention can be expressed together with other structural or regulatory genes to achieve a desired effect. A cell or plant, such as a transformed cell or a transgenic plant, can be transformed, engineered or bred to co-express both LEC2 nucleotide and/or LEC2 polypeptide, and another gene or gene product. Alternatively, two or more LEC2 nucleic acids can be co-expressed together in the same plant or cell.

The LEC2 nucleic acids of the invention, when expressed in plant reproductive or vegetative tissue, can induce ectopic embryo morphogenesis. Thus, in one embodiment, a LEC2 nucleic acid of the invention is expressed in a sense conformation in a transgenic plant to induce the expression of ectopic embryo-like structures. For example, unlike wild type leaves, organs from plants with ectopic embryo-like structures do not expand and do not possess trichomes. Morphologically, these leaf-like structures more closely resemble embryonic cotyledons than leaves.

In another embodiment, LEC2 is co-expressed with a gene or nucleic acid that increases reproductive tissue mass, e.g., increases fruit size, seed mass, seed protein or seed oils. For example, co-expression of antisense nucleic acid to ADC genes, such as AP2 and RAP2 genes of Arabidopsis, will dramatically increase seed mass, seed protein and seed oils; see, e.g., Jofuku, et al., WO 98/07842; Okamuro (1997) *Proc. Natl. Acad. Sci. USA* 94:7076–7081; Okamuro (1997) *Plant Cell* 9:37–47; Jofuku (1994) *Plant Cell* 6:1211–1225. Thus, co-expression of a LEC2 nucleic acid of the invention, to induce ectopic expression of embronic cells and tissues, together with another plant nucleic acid and/or protein, such as the seed-mass enhancing antisense AP2 nucleic acid, generates a cell, tissue, or plant (e.g., a transgenic plant) with increased fruit and seed mass, greater yields of embryonic storage proteins, and the like. Alternatively, coexpression of antisense nucleic acids to LEC2 and LEC1 is useful to inhibit seed production in fruit.

In another embodiment, the LEC2 nucleic acids of the invention are expressed in plant reproductive or vegetative cells and tissues which lack the ability to produce functional ADC genes, such as AP2 and RAP2 genes. The LEC2 nucleic acid can be expressed in an ADC "knockout" transgenic plant. Alternatively, the LEC2 nucleic acid can be expressed in a cell, tissue or plant expressing a mutant ADC nucleic acid or gene product. Expression of LEC2 nucleic acid in any of these non-functioning ADC models will also produce a cell, tissue or plant with increased fruit and seed mass, greater yields of embryonic storage proteins, and the like.

Also, as discussed above, the LEC2 nucleic acids of the invention are useful for the production of apomictic plants. For instance, LEC2 nucleic acids can be expressed in combination with LEC1 nucleic acids as described for instance by Lotan, et al. *Cell* 93:1195–1205 (1998) and in U.S. Ser. No. 09/026,221. Alternatively, FIE (e.g., PCT WO99/09676 and Ohad, N. et al. (1999) *Plant Cell* 11(3):407–16) and/or FUSCA3 (Luerben, H., et al. (1998) *Plant J.* 15:755–764) nucleic acids can also be combined with LEC1 and/or LEC2 nucleic acids. In these embodiments, constructs providing expression of a LEC2 nucleic acid are used in combination with constructs that lead to expression of LEC1 or FUS3 and/or inhibition of FIE expression. Means for targeting expression to desired tissues, such as the female gametophyte or ovules are discussed below.

LEC2 Gene Fusions

LEC2 nucleic acid sequences also include fusions between two or more LEC2 genes. Different domains of different genes can be fused. LEC2 gene fusions can be linked directly or can be attached by additional amino acids that link the two of more fusion partners.

Gene fusions can be generated by basic recombinant DNA techniques as described below. Selection of gene fusions will depend on the desired phenotype caused by the gene fusion. For instance, if phenotypes associated with the domain of one LEC2 protein are desired with phenotypes associated with a different domain of a second LEC2 protein, a fusion of the first LEC2 protein's domain to the second LEC2's domain would be created. The fusion can subsequently be tested in vitro or in vivo for the desired phenotypes.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

EXAMPLES

The following examples are offered to illustrate, but no to limit the claimed invention.

Example 1

This example shows the identification and isolation of the LEC2 gene.

The lec2-1 allele was derived from a population of Ws-0 ecotype plants mutagenized with T-DNA (Feldmann, K. A., et al. (1987). *Mol. Gen. Genet.* 208:1–9). The LEC2 gene, however, is not tagged in this plant line. Other untagged mutant alleles of the LEC2 gene in the Ws-4 ecotype, DLM1, CUC3, and CPT9, were obtained from the Institut National de la Recherche Agronomique.

LEC2 was mapped genetically on the basis of its position in chromosome 1. Recombinants were identified with DISTORTED1 (DIS1) and DIS2 in the Ler ecotype, which map approximately 17 cm north and 5 cM south of LEC2, respectively. FIG. 1 shows the details of the mapping strategy, including the number of recombinants between LEC2 and each of the markers.

LEC2 was mapped to bacterial artificial chromosome (BAC) clone F1A10. Mapping of the ends of cosmid clones prepared from this BAC narrowed the region containing LEC2 to a 23 kb region. A cosmid library was prepared from BAC F1A10 DNA. A 9 kb BamHI fragment from cosmid 80 of this library in this 23 kb region was hybridized to a gel blot containing genomic DNAs from wild type Ws-0 and Ws-4 and the lec2 mutants, i.e. lec2-1, DLM1, CUC3, and CPT9. The blot identified a 3 kb EcoRI restriction fragment in wild type plants that was polymorphic in the lec2-1 and CPT9 genome, indicating the LEC2 was likely to comprise at least a part of this fragment.

To confirm this hypothesis, nucleotide sequencing of the 3 kb EcoRI fragment and partial sequencing of the 9 kb BamHI fragment revealed that the 3 kb EcoRI fragment contains the 5' region of a gene as predicted by Genscan analysis program (http://CCR-081.mit.edu/GENSCAN.html). Analyses of this sequence using Blast searches of public databases (http://www.ncbi.nlm.nih.gov/BLAST/) revealed an unordered and unannotated partial sequence of BAC F3H9 (see FIG. 1). A contiguous region of nucleotide sequence from this BAC corresponded to part of the 3 kb EcoRI fragment and provided the 3' end of the gene.

Blast analysis of the LEC2 gene sequence (SEQ ID NO:1) revealed homology to the B3 domain of FUS3 and ABI3. Thus, LEC2 is a transcriptional regulator of embryo development. The amino acid sequence of the polypeptide encoded by LEC2 is approximately 56% identical to FUS3 over 103 amino acids. The identities are across the B3 domain of FUS3 (Genbank Accession number AF016265.1). The highest identity found in the BLAST search was a 60% identity over 95 amino acids with the B3 domain of carrot C-ABI-3 protein (Genbank Accession number AB005558.1).

Amino acid residues 165 to 277 of SEQ ID NO:2 represent the B3 domain of LEC2. The B3 domain of LEC2 is encoded by positions 3682–3690, 3848–3922, 4817–4917, 5101–5147, 5257–5330 and 5679–5681 of SEQ ID NO:1.

A molecular analysis of the genomic sequence (SEQ ID NO:1) reveals many features. For example, the ATG start codon is at position 3196 and the stop codon is at position 5973. The end of the cDNA is at position 6166. There are six exons in the gene. The positions of the exons in SEQ ID NO:1 are: 3196–3690, 3848–3922, 4817–4917, 5101–5147, 5257–5330, and 5679–5975.

Example 2

This example shows nucleotide sequencing of two mutant alleles of LEC2. Both mutants have deletions in the region of the coding sequence that encodes the B3 domain.

Nucleotide sequencing of the LEC2 allele of the mutant CUC3 revealed an 11 base pair deletion compared to the wild type LEC2 sequence. This deletion results in an alteration of the reading frame and thus the resultant mutant phenotype.

Nucleotide sequencing of the LEC2 allele of the mutant DLM1 revealed a 33 base pair deletion compared to the wild type LEC2 sequence. This deletion is the cause of the mutant phenotype.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid comprising a polynucleotide sequence, or complement thereof, encoding a LEC2 polypeptide exhibiting at least 65% sequence identity to SEQ ID NO:2, with the proviso that the nucleic acid is not bacterial artificial chromosome clone F3H9, wherein the polynucleotide induces ectopic somatic embryogenesis or inhibits embryogenesis when expressed in a plant.

2. The isolated nucleic acid of claim 1, wherein the polypeptide is SEQ ID NO:2.

3. The isolated nucleic acid of claim 1, wherein the polynucleotide sequence is SEQ ID NO:1.

4. The isolated nucleic acid of claim 1, wherein the nucleic acid further comprises a promoter operably linked to the polynucleotide.

5. The isolated nucleic acid of claim 4, wherein the promoter is a constitutive promoter.

6. The isolated nucleic acid of claim 4, wherein the promoter comprises SEQ ID NO:3.

7. The isolated nucleic acid of claim 4, wherein the promoter comprises SEQ ID NO:4.

8. The isolated nucleic acid of claim 4, wherein the polynucleotide sequence is linked to the promoter in an antisense orientation.

9. An isolated nucleic acid molecule comprising a polynucleotide sequence exhibiting at least 65% sequence identity to SEQ ID NO:1, with the proviso that the nucleic acid is not bacterial artificial chromosome clone F3149, wherein the polynucleotide induces ectopic somatic embryogenesis or inhibits embryogenesis when expressed in a plant.

10. An expression cassette comprising a promoter operably linked to a heterologous polynucleotide sequence, or a complement thereof, encoding a LEC2 polypeptide exhibiting at least 85% sequence identity to SEQ ID NO:2, wherein the polynucleotide induces ectopic somatic embryogenesis or inhibits embryogenesis when expressed in a plant.

11. The expression cassette of claim 10, wherein the LEC2 polypeptide is SEQ ID NO:2.

12. The expression cassette of claim 11, wherein the polynucleotide sequence is SEQ ID NO:1.

13. The expression cassette of claim 10, wherein the promoter is a constitutive promoter.

14. The expression cassette of claim 10, wherein the promoter comprises SEQ ID NO:3.

15. The expression cassette of claim 10 wherein the promoter comprises a polynucleotide SEQ ID NO:4.

16. The expression cassette of claim 10, wherein the polynucleotide sequence is linked to the promoter in an antisense orientation.

17. An expression cassette for the expression of a heterologous polynucleotide in a plant cell, wherein the expression cassette comprises a promoter comprising SEQ ID NO:3 and wherein the promoter is operably linked to a heterologous polynucleotide.

18. The expression cassette of claim 17, wherein the promoter further comprises a polynucleotide comprising SEQ ID NO:4.

19. A host cell comprising an exogenous polynucleotide sequence, or complement thereof, encoding a LEC2 polypeptide exhibiting at least 65% sequence identity to SEQ ID NO:2, with the proviso that the nucleic acid is not bacterial artificial chromosome clone F3H9, wherein the polynucleotide induces ectopic somatic embryogenesis or inhibits embryogenesis when expressed in a plant.

20. The host cell of claim 19, wherein the polynucleotide further comprises a promoter operably linked to the polynucleotide sequence.

21. The host cell of claim 20, wherein the promoter is constitutive.

22. The host cell of claim 20; wherein the promoter comprises SEQ ID NO:3.

23. The host cell of claim 20, wherein the promoter comprises SEQ ID NO:4.

24. The host cell of claim 19, wherein the cell is a plant cell.

25. The host cell of claim 19, wherein the cell is a bacterial cell.

26. The host cell of claim 19, wherein the cell is a yeast cell.

27. A method of introducing an isolated nucleic acid into a host cell comprising:
    (a) providing an isolated nucleic acid according to claim 1; and
    (b) contacting the nucleic acid with the host cell under conditions that permit insertion of the nucleic acid into the host cell.

28. A method of inducing somatic embryogenesis or inhibiting embryogenesis in a plant, the method comprising,
    introducing into a plant cell an expression cassette comprising a promoter operably linked to a heterologous LEC2 polynucleotide, the heterologous LEC2 polynucleotide encoding a LEC2 polypeptide at least 65% identical to SEQ ID NO:2; and
    identifying a plant regenerated from the plant cell, wherein the plant exhibits somatic embryogenesis or inhibited embryogenesis.

29. The method of claim 28, wherein the LEC2 polynucleotide encodes SEQ ID NO:2.

30. The method of claim 29, wherein the LEC2 polynucleotide is SEQ ID NO:1.

31. The method of claim 28, wherein the expression cassette is introduced by Agrobacterium.

32. The method of claim 28, wherein the expression cassette is introduced by a sexual cross.

33. The method of claim 28, wherein somatic embryogenesis is induced in the plant.

34. The method of claim 28, wherein seed storage proteins are induced in the plant.

35. The method of claim 28, wherein a plant is regenerated from the plant cell.

36. A transgenic plant cell or transgenic plant comprising an exogenous polynucleotide sequence, or complement thereof, encoding a LEC2 polypeptide exhibiting at least 65% sequence identity to SEQ ID NO:2, wherein the polynucleotide induces ectopic somatic embryogenesis or inhibits embryogenesis when expressed in a plant.

37. The transgenic plant cell or transgenic plant of claim 36, wherein the LEC2 polypeptide is SEQ ID NO:2.

38. The transgenic plant cell or transgenic plant of claim 37, wherein the polynucleotide sequence is SEQ ID NO:1.

39. The transgenic plant cell or transgenic plant of claim 36, wherein the nucleic acid further comprises a promoter operably linked to the polynucleotide sequence.

40. The transgenic plant cell or transgenic plant of claim 39, wherein the promoter is a constitutive promoter.

41. The transgenic plant cell or transgenic plant of claim 36, wherein the promoter comprises SEQ ID NO:3.

42. The transgenic plant cell or transgenic plant of claim 36, wherein the promoter comprises SEQ ID NO:4.

43. The transgenic plant cell or transgenic plant of claim 36, wherein the polynucleotide sequence is linked to the promoter in an antisense orientation.

44. A plant which has been regenerated from a plant cell according to 36.

45. The method of claim 28, wherein the detecting step comprises detecting a plant regenerated from the plant cell characterized by inhibited embryogenesis.

46. The method of claim 28, wherein the detecting step comprises detecting a plant regenerated from the plant cell characterized by somatic embryogenesis.

47. The host cell of claim 19, wherein the host cell comprises an expression cassette comprising a promoter operably linked to a heterologous polynucleotide sequence, or a complement thereof, encoding a LEC2 polypeptide exhibiting at least 65% sequence identity to SEQ ID NO:2, and wherein the polynucleotide induces ectopic somatic embryogenesis or inhibits embryogenesis when expressed in a plant.

48. The isolated nucleic acid of claim 1, wherein the LEC2 polypeptide exhibits at least 80% sequence identity to SEQ ID NO:2.

49. The isolated nucleic acid of claim 1, wherein the LEC2 polypeptide exhibits at least 95% sequence identity to SEQ D NO:2.

50. The expression cassette of claim 10, wherein the LEC2 polypeptide exhibits at least 80% sequence identity to SEQ ID NO:2.

51. The expression cassette of claim 10, wherein the LEC2 polypeptide exhibits at least 95% sequence identity to SEQ ID NO:2.

52. The host cell of claim 19, wherein the LEC2 polypeptide exhibits at least 80% sequence identity to SEQ ID) NO:2.

53. The host cell of claim 19, wherein the LEC2 polypeptide exhibits at least 95% sequence identity to SEQ ID NO:2.

54. The method of claim 28, wherein the LEC2 polypeptide exhibits at least 80% sequence identity to SEQ 1D NO:2.

55. The method of claim 28, wherein the LEC2 polypeptide exhibits at least 95% sequence identity to SEQ ID NO:2.

56. The transgenic plant cell or plant of claim 36, wherein the LEC2 polypeptide exhibits at least 80% sequence identity to SEQ ID NO:2.

57. The transgenic plant cell or plant of claim 36, wherein the LEC2 polypeptide exhibits at least 95% sequence identity to SEQ ID NO:2.

* * * * *

UNITED STATES PATENT AND TRADEMARK OFFICE
CERTIFICATE OF CORRECTION

PATENT NO. : 6,492,577 B1
DATED : December 10, 2002
INVENTOR(S) : Harada et al.

It is certified that error appears in the above-identified patent and that said Letters Patent is hereby corrected as shown below:

Column 43,
Line 43, please delete "F3149" and insert -- F3H9 --.

Signed and Sealed this

Thirtieth Day of September, 2003

JAMES E. ROGAN
*Director of the United States Patent and Trademark Office*

SEQUENCE LISTING

```
<160> NUMBER OF SEQ ID NOS: 14

<210> SEQ ID NO 1
<211> LENGTH: 6766
<212> TYPE: DNA
<213> ORGANISM: Arabidopsis sp.
<220> FEATURE:
<223> OTHER INFORMATION: LEAFY COTYLEDON2 (LEC2) genomic sequence
<221> NAME/KEY: misc_feature
<222> LOCATION: (3196)..(3198)
<223> OTHER INFORMATION: ATG start codon
<221> NAME/KEY: exon
<222> LOCATION: (3196)..(3690)
<221> NAME/KEY: exon
<222> LOCATION: (3848)..(3922)
<221> NAME/KEY: exon
<222> LOCATION: (4817)..(4917)
<221> NAME/KEY: exon
<222> LOCATION: (5101)..(5147)
<221> NAME/KEY: exon
<222> LOCATION: (5257)..(5330)
<221> NAME/KEY: exon
<222> LOCATION: (5679)..(5975)
<221> NAME/KEY: misc_feature
<222> LOCATION: (6166)
<223> OTHER INFORMATION: cDNA end

<400> SEQUENCE: 1
atatatatat atatatatat atatatatat ctttgagttc atgattttt tacaagaaga      60 ctatatagtt ggtgatatgt actctcacaa cattttgtta agaattctcc aaaaacttat    120
atgtcatctt acgaaaattg ttaaacatca aacagtcaca tttgtaaaaa gctaattaca    180
acaacattta ttaacagtta aaatataaat ctcttaggta gcccggatta aaactcttaa    240
ttcaattgtt acatatatat tcgggagtag tccaaatttt cttctaatct aatataataa    300
agtaatgcta ttcttaagaa caagttttga gaaactgaca tgtagatata gaactctaaa    360
tatattatcc taagaagcta tggatttact aatttcatcc tatccctatg tgaatcccta    420
```

```
aactcaacga gagcattact aagacatgat catagaagca tatatcatat ttgaataaaa      480
ttacataaat aattcaaaag attatagagt ttagaaagta ttattttctt tataaggttt      540
tgaaatctct aaagaattct tgaaaaatag aaaacaaaaa gtaaaagctt gataattcta      600
actattgacc caaatatat taataggttc tcaaaaacat ttaggaacaa ataatgcaaa      660
tacaaaaatc ttatgggaca attatgtaat cttctaattt ttaaactggg aagacttttg      720
ttgggatgcg aacggtgtct atcgacatgt cgatcgacat tgattacttg atctgacacc      780
aaattcgttt tttcagcctt tattttccg tttggttcca aaatacttaa cgaactccaa      840
atatattcgc ataaataacc gaaaagattt ttaaaataac atagtaactc taaaaacaat      900
atctatatca taaataataa cggaaaataa tccatgatat atcaattata actcaaccaa      960
agccaacgaa caaaaaacat gaagcaaagc tacatatact actaatgata agtctaaatc     1020
gtcttcgaca tatctaacaa aaccaaaata tatatacttg gaaacaactt cttcacccgg     1080
acacaaattt ctcaaagcaa gtgtcaaaaa ctctacgata taacaaaca gagtatatgt      1140 agctatgcaa tccaaggagc tttcctcttg tctaaaagtg tcataatggc ggaccggtcg     1200
caatcttatg tagctctacg ctacccctttt tggctacgga aggtgcttga aattgataaa     1260
tacattacat tgttgtaatg attttctgta gtttgattgc ttttgtttcc tctttgtaat     1320
tgtgaacaag ttgttgttaa tatcatgaat cattcagaca gaaaaaaaaa aataacaaac     1380
agagaaaaat cccaaaaaat aagaaaatat agatgacgct acatcactat atttcccta      1440 cctccttagt ctcgctagga gttacgagtc gtgcgcctct tccagtattt gccataatta     1500
actgagtggg atctttttgt ccatcaaccc atgcctcttc aatatttttt actaatccac     1560
catttccttc cattgttatt gatatatatg tttcaccaaa tatacctata caaaactata     1620
tttcaaactt ataacgaaca agaaaacgag tttttcaaaa tttcagagtt tatggccgag     1680
aataaacatg agctcggcgg ccgcggttta gaacaaaatt tgtgtccatc tcctcgccaa     1740
atgtaagttt ctgatagagc ataacattgg gttgggacga aaaaggaaac caataagatg     1800
atagaaattg ctgggtaatt ggaggtgttc ttagggcacg agttgaacat gttaccaaac     1860
ctaattcatg gttagaaatt tggtgacagt caagcttata ttatctttga taactatgtt     1920
tctagttgtt tcattattag tatagaaaaa actttgtttt gtagagtgtt ctatgggtta     1980
tgatttcgaa aagaaaaaaa ttgtgagaca cctaataaaa ttatttcgac aaaaaaaata     2040
gcttgtataa aaaaatcaga ttttaattta tgtttgaaca aattccaata gttaaaaata     2100
attatttgtt ccgattaatc gagttttgca aaatatgcac aaaatctatc atcgtaccat     2160
ttctaagact atatatttgg ttatatattt tatgccgtgt tctgattcca aaaatttta      2220 gcgcatagta aattttctaa aaagcaaaat tttctcaaaa gtgtactaat gacaattaat     2280
tgagtttcta caaaataaga ataactattg actcgatttt cacaaaatta gtatgctaaa     2340
tatcacatta cttttaaaat taaatggaat tgtcttttc aatattggat acgaataatt      2400
tttacactaa agtatttta ataaaataac cgtttattca aaatatgtaa agacgacaaa      2460
aatatatatt aaatggaaaa acgactaact tagttttgc aaaataaaat ggatttgtcc      2520
ttttcaatgt ttgaatacaa aaaaaaatct ataataagtt tattatatta aaataacccg     2580
ttttttcaga atacgcaaaa acgacaaaaa aatattaatt acaaagaaat ttagtttata     2640
caaaaatatg aatggctatt aatggtgttt actctaaattt taattattat gcatttatgc    2700
taaatctttc taaaggtaca aagattcgtt ttttcaatgt ttgaactgca tattaaggta     2760
```

```
tagatttgga ccttaacaga gttaatatat aaggaagaga gccaaggaac tccaaaataa      2820
aataaagagc cttctctctc tctctctgag aaaaaacaca tatagccaat gaccttctcg      2880
tggtcttctg tgccataaaa gccattatat acattcaaac acaatctggc gccacatata      2940
cacatgtact agtgtatgta tatgtcctaa cctctgtatt catatctctc tccttgtctg      3000
agtggtgcga tgggtatccc cataagctgc aaacattgaa ccatctgcaa cattttgact      3060
cgttttcttt tgtgtttttc aacatctgt ctcttcttca ctcgctctct cctaatcaat      3120
ctccccaacg acctctcttt tttttgttt cttcactcag atctctctcc ctctctctct      3180
ctctctccgg gaaaaatgga taacttctta cccttttccct cttctaacgc aaactctgtc      3240
caagaactct ctatggatcc taacaacaat cgctcgcact tcacaacagt ccctacttat      3300
gatcatcatc aggctcagcc tcatcacttc ttgcctccgt tttcataccc ggtggagcag      3360
atggcggcgg tgatgaatcc tcagccggtt tacttatcgg agtgttatcc tcagatcccg      3420
gttacgcaaa ccggaagtga attcggttct ctggttggta atccttgttt gtggcaagag      3480
agaggtggtt ttcttgatcc gcgtatgacg aagatggcaa ggatcaacag gaaaaacgcc      3540
atgatgagat caagaaacaa ctctagccct aattctagtc caagtgagtt ggttgattca      3600
aagagacagc tgatgatgct taacttgaaa aataacgtgc agatctccga caagaaagat      3660
agctaccaac agtccacatt tgataacaag gtttggtttt ttttcgtccc aattttttgaa      3720 tatgtacgat tttcttattt attttttggt tttcatgtta ttatatgaat atatacaatt      3780
ttgggtgtat aaaactttat gatacaattt ttaattattt ttattttgtt ttggttgttg      3840
cttgtagaag cttagggttt tgtgtgagaa ggaattgaag aacagcgatg ttgggtcact      3900
cgggaggata gttctaccaa aggtatgtga attcttaaaa ttcttttttaa tttctcgaac      3960 caatacttgg taaaaaattc tgtttgtttt catgattttt cttcttttttc tgttattgta      4020 taatgataaa tgaaatgcat tgatgaaaat gataatcatc aatcacgtac gtcattgaaa      4080
atttaaaaca caatcccata aaaaaattct tagaagaata aagttatttt atgaggatta      4140
gacttccgtc attttataca agagatttat ggaacacaag cacaaaaatc gttgcggcca      4200
catattatct cattattcaa tttcactgag ttttttcttgc acatttcatt ttactttcaa      4260 atttttacata atatgtttat ctaactgttt tctgtttaac caataaaaag ttttaagtct      4320
ttaaaataag tatccacacg aaaacaagat gaataagaaa catgagaaga aaatgtggac      4380
tgaagtaaag ttagtttaat caaattttgt ttggttttctg tacgaacttt tatgtttttg      4440
attttttatt tatttagcaa gtagtatatg aattaattta atttttttata gttttaaact      4500 tgatttttttt aaagatagct tataattatt gaatatatgg aatgctactt cttccttcaa      4560
tgttgttatt tgtatttgtt aaatttgaaa ttgggttgaa gaaaatgaaa ggtcgtttat      4620
atgcctttcc taattaattg tccattgaat ggtttaccac tttacctcga aaaagtgaat      4680
aaataaaaat cattagggaa aaagattcta catatcttgg ggtttttatca aactttttaat      4740 caattttatt ttaatgatat cgttcttatt tttcttagca agacactaat acgtgaatca      4800
tggctttgga atgcagagag atgcagaagc aaatcttccg aagctatctg ataaagaagg      4860
aatcgttgta cagatgagag atgttttctc tatgcagtct tggtctttca aatacaagta      4920
aataattcgc tttctaatcc attttttcatt tcccaattaa cacaaccttaa attttatgct      4980 caactgttag tccctttttg tgttaccggt tctcatactt agtttttaaat tttgattttt      5040 ttttatcaat tgggaacagt attataatta gaagactaaa tgctcgtatt aatgacatag      5100
gttttggtcc aataacaaga gcagaatgta tgtcctcgag aacacaggta aattaaggag      5160
```

-continued

```
ctccaatatt atttcaaaag tacaaaatct tatgtaaaac tactttttaaa taaatatgat      5220 ttaccttttc cttttttttt gtggtgataa ctaaaggaga atttgtgaag caaaatggag      5280
ctgagatagg agactttta acaatatacg aggacgaaag caagaatctc gtgagctctc      5340
tatttacttc atttccctat ttaattttgt aaaaagacat gaaaaagtta aaaaaaaatg      5400
attaattagt agtccaaaat tggaaattta aaaagtggtc tttgaattga gtttgttaag      5460
catccagaca aaagttttaa aaccttttc tgtcaatgat aactgttctt atatggtagg      5520
tattaataac ttgtgggcct agggggaagt aaatactatg gagaaaattt tataataatt      5580
gaaatttggt taatttagag tttataatat ggtttgattt ggtttggtta ggacttatga      5640
cttatgtgtg tgtgtgtgat cgcttgttct tattacagta cttcgccatg aatgaaattt      5700
cgggaaaaca aaatgaagga agagaaaatg agtcgaggga aaggaaccac tacgaagagg      5760
caatgcttga ttacatacca agagacgaag aggaagcttc cattgcaatg ctcatcggaa      5820
atctaaacga tcactatccc atccctaacg atctcatgga cctcaccact gaccttcagc      5880
accatcaagc cacgtcctca atgacacctg aggatcacgc gtacgtgggt tcatccgatg      5940
atcaggtgag ctttaacgac tttgagtggt ggtgatatgg tggtggaagt tctcaagttc      6000
ataaccccct tatgaaaata gaccttaaga tatacaaaag agattaaaag aaaaaaaagt      6060
tagtatattt catcatatct ctcattgaag atgagattta tatctataat tgttttatat      6120
agtgttttta ttacttttct atcaatatat taaagttttta attaataaaa acgatcattt      6180
atcttcagta taattagttt ttaattacaa acaaaattat tctgagtttt atcacccaga      6240
agagattatc gacatcttgt tagcaaaaaa ccattaaaaa acacattagc acaattagag      6300
atatggactt tcgtctttcg ggatttccca aatagttgat attccgttac aaataatgga      6360
acgacatagg tgctggattg gttataacgt tcatagctaa cttgtaagaa ttgtcgaaaa      6420
cttttgaatt tgttaaaaaa gaaatgaca attaaagtgt ttataatatg ttactagtgt      6480
gaaattatgt atcaatttt tttttgttaaa aaaatcattt tgtttctatt tagaaattta      6540
acgataactt gggaacactg ccttgcctta cacgcgatga agggtactat cgcctacaag      6600
ttttcttttt tcatttgttt tttggtcggc acctacaagt ttttctaaaa aggatgatgc      6660
atagtagtcg ccggtgggta atactaatag ctttctatc agacaaaaaa acatatgatt      6720
tttgttttct tatttgctaa ttagaaaatc aagataagtt aagagg               6766
```

<210> SEQ ID NO 2
<211> LENGTH: 362
<212> TYPE: PRT
<213> ORGANISM: Arabidopsis sp.
<220> FEATURE:
<223> OTHER INFORMATION: LEAFY COTYLEDON2 (LEC2) polypeptide
<221> NAME/KEY: DOMAIN
<222> LOCATION: (165)..(277)
<223> OTHER INFORMATION: B3 DNA binding domain

<400> SEQUENCE: 2

```
Met Asp Asn Phe Leu Pro Phe Pro Ser Ser Asn Ala Asn Ser Val Gln
  1               5                  10                  15

Glu Leu Ser Met Asp Pro Asn Asn Asn Arg Ser His Phe Thr Thr Val
             20                  25                  30

Pro Thr Tyr Asp His His Gln Ala Gln Pro His His Phe Leu Pro Pro
         35                  40                  45

Phe Ser Tyr Pro Val Glu Gln Met Ala Ala Val Met Asn Pro Gln Pro
     50                  55                  60
```

```
Val Tyr Leu Ser Glu Cys Tyr Pro Gln Ile Pro Val Thr Gln Thr Gly
 65                  70                  75                  80

Ser Glu Phe Gly Ser Leu Val Gly Asn Pro Cys Leu Trp Gln Glu Arg
                 85                  90                  95

Gly Gly Phe Leu Asp Pro Arg Met Thr Lys Met Ala Arg Ile Asn Arg
            100                 105                 110

Lys Asn Ala Met Met Arg Ser Arg Asn Asn Ser Ser Pro Asn Ser Ser
        115                 120                 125

Pro Ser Glu Leu Val Asp Ser Lys Arg Gln Leu Met Met Leu Asn Leu
    130                 135                 140

Lys Asn Val Gln Ile Ser Asp Lys Lys Asp Ser Tyr Gln Ser
145                 150                 155                 160

Thr Phe Asp Asn Lys Lys Leu Arg Val Leu Cys Glu Lys Glu Leu Lys
                165                 170                 175

Asn Ser Asp Val Gly Ser Leu Gly Arg Ile Val Leu Pro Lys Arg Asp
            180                 185                 190

Ala Glu Ala Asn Leu Pro Lys Leu Ser Asp Lys Glu Gly Ile Val Val
        195                 200                 205

Gln Met Arg Asp Val Phe Ser Met Gln Ser Trp Ser Phe Lys Tyr Lys
    210                 215                 220

Phe Trp Ser Asn Asn Lys Ser Arg Met Tyr Val Leu Glu Asn Thr Gly
225                 230                 235                 240

Glu Phe Val Lys Gln Asn Gly Ala Glu Ile Gly Asp Phe Leu Thr Ile
                245                 250                 255

Tyr Glu Asp Glu Ser Lys Asn Leu Tyr Phe Ala Met Asn Gly Asn Ser
            260                 265                 270

Gly Lys Gln Asn Glu Gly Arg Glu Asn Glu Ser Arg Glu Arg Asn His
        275                 280                 285

Tyr Glu Glu Ala Met Leu Asp Tyr Ile Pro Arg Asp Glu Glu Ala
    290                 295                 300

Ser Ile Ala Met Leu Ile Gly Asn Leu Asn Asp His Tyr Pro Ile Pro
305                 310                 315                 320

Asn Asp Leu Met Asp Leu Thr Thr Asp Leu Gln His His Gln Ala Thr
                325                 330                 335

Ser Ser Met Thr Pro Glu Asp His Ala Tyr Val Gly Ser Ser Asp Asp
            340                 345                 350

Gln Val Ser Phe Asn Asp Phe Glu Trp Trp
        355                 360
```

<210> SEQ ID NO 3
<211> LENGTH: 3195
<212> TYPE: DNA
<213> ORGANISM: Arabidopsis sp.
<220> FEATURE:
<223> OTHER INFORMATION: LEC2 5' promoter, 5' untranslated region

<400> SEQUENCE: 3

```
atatatatat atatatatat atatatatat ctttgagttc atgatttttt tacaagaaga    60
ctatatagtt ggtgatatgt actctcacaa cattttgtta agaattctcc aaaaacttat   120
atgtcatctt acgaaaattg ttaaacatca aacagtcaca tttgtaaaaa gctaattaca   180
acaacattta ttaacagtta aaatataaat ctcttaggta gcccggatta aaactcttaa   240
ttcaattgtt acatatatat tcgggagtag tccaaatttt cttctaatct aatataataa   300
agtaatgcta ttcttaagaa caagttttga gaaactgaca tgtagatata gaactctaaa   360
```

```
tatattatcc taagaagcta tggatttact aatttcatcc tatccctatg tgaatcccta    420
aactcaacga gagcattact aagacatgat catagaagca tatatcatat ttgaataaaa    480
ttacataaat aattcaaaag attatagagt ttagaaagta ttattttctt tataaggttt    540
tgaaatctct aaagaattct tgaaaaatag aaaacaaaaa gtaaaagctt gataattcta    600
actattgacc caaatatat taataggttc tcaaaaacat ttaggaacaa ataatgcaaa    660
tacaaaaatc ttatgggaca attatgtaat cttctaattt ttaaactggg aagacttttg    720
ttgggatgcg aacggtgtct atcgacatgt cgatcgacat tgattacttg atctgacacc    780
aaattcgttt tttcagcctt tattttccg tttggttcca aaatacttaa cgaactccaa    840
atatattcgc ataataacc gaaagatttt ttaaaataac atagtaactc taaaaacaat    900
atctatatca taaataataa cggaaaataa tccatgatat atcaattata actcaaccaa    960
agccaacgaa caaaaaacat gaagcaaagc tacatatact actaatgata agtctaaatc    1020
gtcttcgaca tatctaacaa aaccaaaata tatatacttg gaaacaactt cttcacccgg    1080
acacaaattt ctcaaagcaa gtgtcaaaaa ctctacgata taacaaaca gagtatatgt    1140 agctatgcaa tccaaggagc tttcctcttg tctaaaagtg tcataatggc ggaccggtcg    1200
caatcttatg tagctctacg ctacccctt tggctacgga aggtgcttga aattgataaa    1260
tacattacat tgttgtaatg attttctgta gtttgattgc ttttgtttcc tctttgtaat    1320
tgtgaacaag ttgttgttaa tatcatgaat cattcagaca gaaaaaaaaa aataacaaac    1380
agagaaaaat cccaaaaaat aagaaaatat agatgacgct acatcactat atttccccta    1440
cctccttagt ctcgctagga gttacgagtc gtgcgcctct tccagtattt gccataatta    1500
actgagtggg atctttttgt ccatcaaccc atgcctcttc aatattttt actaatccac    1560 catttccttc cattgttatt gatatatatg tttcaccaaa tatacctata caaaactata    1620
tttcaaactt ataacgaaca agaaaacgag ttttcaaaa tttcagagtt tatggccgag    1680
aataaacatg agctcggcgg ccgcggttta gaacaaaatt tgtgtccatc tcctcgccaa    1740
atgtaagttt ctgatagagc ataacattgg gttgggacga aaaggaaac caataagatg    1800 atagaaattg ctgggtaatt ggaggtgttc ttagggcacg agttgaacat gttaccaaac    1860
ctaattcatg gttagaaatt tggtgacagt caagcttata ttatctttga taactatgtt    1920
tctagttgtt tcattattag tatagaaaaa actttgtttt gtagagtgtt ctatgggtta    1980
tgatttcgaa aagaaaaaaa ttgtgagaca cctaataaaa ttatttcgac aaaaaaaata    2040
gcttgtataa aaaatcaga ttttaattta tgtttgaaca aattccaata gttaaaaata    2100
attatttgtt ccgattaatc gagttttgca aaatatgcac aaaatctatc atcgtaccat    2160
ttctaagact atatatttgg ttatatattt tatgccgtgt tctgattcca aaaattttta    2220
gcgcatagta aattttctaa aaagcaaaat tttctcaaaa gtgtactaat gacaattaat    2280
tgagtttcta caaataaga ataactattg actcgatttt cacaaaatta gtatgctaaa    2340
tatcacatta cttttaaaat taaatggaat tgtcttttc aatattggat acgaataatt    2400
tttacactaa agttatttta ataaaataac cgtttattca aaatatgtaa agacgacaaa    2460
aatatatatt aaatgaaaa acgactaact tagttttgc aaaataaaat ggatttgtcc    2520
ttttcaatgt ttgaatacaa aaaaaatct ataataagtt tattatatta aataacccg    2580 ttttttcaga atacgcaaaa acgacaaaaa aatattaatt acaagaaat ttagtttata    2640 caaaaatatg aatggctatt aatggtgttt actctaaatt taattattat gcatttatgc    2700
```

-continued

| | |
|---|---|
| taaatctttc taaaggtaca aagattcgtt ttttcaatgt ttgaactgca tattaaggta | 2760 |
| tagatttgga ccttaacaga gttaatatat aaggaagaga gccaaggaac tccaaaataa | 2820 |
| aataaagagc cttctctctc tctctctgag aaaaaacaca tatagccaat gaccttctcg | 2880 |
| tggtcttctg tgccataaaa gccattatat acattcaaac acaatctggc gccacatata | 2940 |
| cacatgtact agtgtatgta tatgtcctaa cctctgtatt catatctctc tccttgtctg | 3000 |
| agtggtgcga tgggtatccc cataagctgc aaacattgaa ccatctgcaa cattttgact | 3060 |
| cgttttcttt tgtgtttttc caacatcgt ctcttcttca ctcgctctct cctaatcaat | 3120 |
| ctccccaacg acctctcttt tttttgttt cttcactcag atctctctcc ctctctctct | 3180 |
| ctctctccgg gaaaa | 3195 |

<210> SEQ ID NO 4
<211> LENGTH: 1000
<212> TYPE: DNA
<213> ORGANISM: Arabidopsis sp.
<220> FEATURE:
<223> OTHER INFORMATION: LEC2 3' promoter, 3' untranslated region

<400> SEQUENCE: 4

| | |
|---|---|
| aataaaaacg atcatttatc ttcagtataa ttagttttta attacaaaca aaattattct | 60 |
| gagtttttatc acccagaaga gattatcgac atcttgttag caaaaaacca ttaaaaaaca | 120 |
| cattagcaca attagagata tggactttcg tctttcggga tttcccaaat agttgatatt | 180 |
| ccgttacaaa taatggaacg acataggtgc tggattggtt ataacgttca tagctaactt | 240 |
| gtaagaattg tcgaaaactt ttgaatttgt taaaaagaa aatgacaatt aaagtgttta | 300 |
| taatatgtta ctagtgtgaa attatgtatc aattttttt tgttaaaaaa atcattttgt | 360 |
| ttctatttag aaatttaacg ataacttggg aacactgcct tgccttacac gcgatgaagg | 420 |
| gtactatcgc ctacaagttt tcttttttca tttgtttttt ggtcggcacc tacaagtttt | 480 |
| tctaaaaagg atgatgcata gtagtcgccg gtgggtaata ctaatagctt ttctatcaga | 540 |
| caaaaaaaca tatgattttt gttttcttat ttgctaatta gaaatcaag ataagttaag | 600 |
| aggccttgat tccctaaacc ctagccctct aacgctagcc tagattctaa tccaagccca | 660 |
| aaactattac tagtataact ctgagtatat ccgagctctt ataactattg cccatactct | 720 |
| atttatagct agcccaacag aattactcaa tactccaaac ccaatagtct aaccctacct | 780 |
| gggatactac actgatcagt tagccctgac agaaaccagt tgacaaaaat accgaacctt | 840 |
| catgaaactg aaaataatag agataaaagg ttcatgcaat acgtaggttt gatttacaat | 900 |
| ccgctattgt aattagtttt caatcgtttt tgtgaaaatg aaacatgtaa gtttatcaaa | 960 |
| ttcaacctct tatcaaaacc tatttaattt gaatagatac | 1000 |

<210> SEQ ID NO 5
<211> LENGTH: 1296
<212> TYPE: DNA
<213> ORGANISM: Arabidopsis sp.
<220> FEATURE:
<223> OTHER INFORMATION: LEC2 cDNA

<400> SEQUENCE: 5

| | |
|---|---|
| atggataact tcttacccctt tccctcttct aacgcaaact ctgtccaaga actctctatg | 60 |
| gatcctaaca caatcgctc gcacttcaca acagtcccta cttatgatca tcatcaggct | 120 |
| cagcctcatc acttcttgcc tccgttttca tacccgtgg agcagatggc ggcggtgatg | 180 |
| aatcctcagc cggtttactt atcggagtgt tatcctcaga tcccggttac gcaaaccgga | 240 |

-continued

```
agtgaattcg gttctctggt tggtaatcct tgtttgtggc aagagagagg tggttttctt      300
gatccgcgta tgacgaagat ggcaaggatc aacaggaaaa acgccatgat gagatcaaga      360
aacaactcta gccctaattc tagtccaagt gagttggttg attcaaagag acagctgatg      420
atgcttaact tgaaaaataa cgtgcagatc tccgacaaga aagatagcta ccaacagtcc      480
acatttgata caagaagct tagggttttg tgtgagaagg aattgaagaa cagcgatgtt      540
gggtcactcg ggaggatagt tctaccaaag agagatgcag aagcaaatct tccgaagcta      600
tctgataaag aaggaatcgt tgtacagatg agagatgttt tctctatgca gtcttggtct      660
ttcaaataca gttttggtc caataacaag agcagaatgt atgtcctcga aacacagga       720
gaatttgtga agcaaaatgg agctgagata ggagactttt taacaatata cgaggacgaa      780
agcaagaatc tctacttcgc catgaatgga aattcgggaa acaaaatga aggaagagaa       840
aatgagtcga gggaaaggaa ccactacgaa gaggcaatgc ttgattacat accaagagac      900
gaagaggaag cttccattgc aatgctcatc ggaaatctaa acgatcacta tcccatccct      960
aacgatctca tggacctcac cactgacctt cagcaccatc aagccacgtc ctcaatgaca     1020
cctgaggatc acgcgtacgt gggttcatcc gatgatcagg tgagctttaa cgactttgag     1080
tggtggtgat atggtggtgg aagttctcaa gttcataacc cccttatgaa aatagacctt     1140
aagatataca aaagagatta aagaaaaaa aagttagtat atttcatcat atctctcatt     1200
gaagatgaga tttatatcta taattgtttt atatagtgtt tttattactt ttctatcaat     1260
atattaaagt tttaattaaa aaaaaaaaa aaaaaa                                1296
```

<210> SEQ ID NO 6
<211> LENGTH: 2968
<212> TYPE: DNA
<213> ORGANISM: Arabidopsis sp.
<220> FEATURE:
<223> OTHER INFORMATION: LEC2 gene from translation start site to polyadenylation site

<400> SEQUENCE: 6

```
atggataact tcttaccctt tccctcttct aacgcaaact ctgtccaaga actctctatg       60
gatcctaaca caatcgctc gcacttcaca acagtcccta cttatgatca tcatcaggct      120
cagcctcatc acttcttgcc tccgttttca tacccggtgg agcagatggc ggcggtgatg      180
aatcctcagc cggtttactt atcggagtgt tatcctcaga tcccggttac gcaaaccgga      240
agtgaattcg gttctctggt tggtaatcct tgtttgtggc aagagagagg tggttttctt      300
gatccgcgta tgacgaagat ggcaaggatc aacaggaaaa acgccatgat gagatcaaga      360
aacaactcta gccctaattc tagtccaagt gagttggttg attcaaagag acagctgatg      420
atgcttaact tgaaaaataa cgtgcagatc tccgacaaga aagatagcta ccaacagtcc      480
acatttgata caaggtttg gttttttttc gtcccaattt ttgaatatgt acgattttct      540
tatttatttt ttggttttca tgttattata tgaatatata caattttggg tgtataaaac      600
tttatgatac aattttaat tatttttatt ttgttttggt tgttgcttgt agaagcttag      660
ggttttgtgt gagaaggaat tgaagaacag cgatgttggg tcactcggga ggatagttct      720
accaaaggta tgtgaattct taaaattctt tttaatttct cgaaccaata cttggtaaaa      780
aattctgttt gttttcatga ttttttcttct ttttctgtta ttgtataatg ataaatgaaa      840
tgcattgatg aaaatgataa tcatcaatca cgtacgtcat tgaaaattta aaacacaatc      900
ccataaaaaa attcttagaa gaataaagtt attttatgag gattagactt ccgtcatttt      960
```

-continued

```
atacaagaga tttatggaac acaagcacaa aaatcgttgc ggccacatat tatctcatta    1020
ttcaatttca ctgagttttt cttgcacatt tcattttact ttcaaatttt acataatatg    1080
tttatctaac tgttttctgt ttaaccaata aaaagtttta agtctttaaa ataagtatcc    1140
acacgaaaac aagatgaata agaaacatga gaagaaaatg tggactgaag taaagttagt    1200
ttaatcaaat tttgtttggt ttctgtacga acttttatgt ttttgatttt ttatttattt    1260
agcaagtagt atatgaatta atttaatttt ttatagtttt aaacttgatt tttttaaaga    1320
tagcttataa ttattgaata tatggaatgc tacttcttcc ttcaatgttg ttatttgtat    1380
ttgttaaatt tgaaattggg ttgaagaaaa tgaaaggtcg tttatatgcc tttcctaatt    1440
aattgtccat tgaatggttt accactttac ctcgaaaaag tgaataaata aaaatcatta    1500
gggaaaaaga ttctacatat cttggggttt tatcaaactt ttaatcaatt ttattttaat    1560
gatatcgttc ttatttttct tagcaagaca ctaaatacgtg aatcatggct ttggaatgca    1620
gagagatgca gaagcaaatc ttccgaagct atctgataaa gaaggaatcg ttgtacagat    1680
gagagatgtt ttctctatgc agtcttggtc tttcaaatac aagtaaataa ttcgctttct    1740
aatccatttt tcatttccca attaacacaa ccttaatttt atgctcaact gttagtccct    1800
ttttgtgtta ccggttctca tacttagttt taaattttga ttttttttta tcaattggga    1860
acagtattat aattagaaga ctaaatgctc gtattaatga cataggtttt ggtccaataa    1920
caagagcaga atgtatgtcc tcgagaacac aggtaaatta aggagctcca atattatttc    1980
aaaagtacaa aatcttatgt aaaactactt ttaaataaat atgatttacc ttttcctttt    2040
tttttgtggt gataactaaa ggagaatttg tgaagcaaaa tggagctgag ataggagact    2100
ttttaacaat atacgaggac gaaagcaaga atctcgtgag ctctctattt acttcatttc    2160
cctatttaat tttgtaaaaa gacatgaaaa agttaaaaaa aaatgattaa ttagtagtcc    2220
aaaattggaa atttaaaaag tggtctttga attgagtttg ttaagcatcc agacaaaagt    2280
tttaaaacct ttttctgtca atgataactg ttcttatatg gtaggtatta ataacttgtg    2340
ggcctagggg gaagtaaata ctatggagaa aattttataa taattgaaat ttggttaatt    2400
tagagtttat aatatggttt gatttggttt ggttaggact tatgacttat gtgtgtgtgt    2460
gtgatcgctt gttcttatta cagtacttcg ccatgaatgg aaattcggga aaacaaaatg    2520
aaggaagaga aaatgagtcg agggaaagga accactacga agaggcaatg cttgattaca    2580
taccaagaga cgaagaggaa gcttccattg caatgctcat cggaaatcta aacgatcact    2640
atcccatccc taacgatctc atggacctca ccactgacct tcagcaccat caagccacgt    2700
cctcaatgac acctgaggat cacgcgtacg tgggttcatc cgatgatcag gtgagcttta    2760
acgactttga gtggtggtga tatggtggtg gaagttctca agttcataac cccttatga    2820 aaatagacct taagatatac aaaagagatt aaaagaaaaa aagttagta tatttcatca    2880 tatctctcat tgaagatgag atttatatct ataattgttt tatatagtgt tttattact     2940 tttctatcaa tatattaaag ttttaatt                                      2968
```

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:genomic
      region amplification primer D2F

<400> SEQUENCE: 7

```
tttcagaata cgcaaaaacg ac                                              22

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:genomic
      region amplification primer D2R

<400> SEQUENCE: 8
aactatcctc ccgagtgacc                                                 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:genomic
      region amplification primer Ef

<400> SEQUENCE: 9
agatggcaag gatcaacagg                                                 20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence:genomic
      region amplification primer BlastR

<400> SEQUENCE: 10
cttgctttcg tcctcgtata ttg                                             23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:genomic
      region amplification primer F2F

<400> SEQUENCE: 11
tttgtgaagc aaaatggagc                                                 20

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence:genomic
      region amplification primer Stop

<400> SEQUENCE: 12
cggatgaacc cacgtacg                                                   18

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:cDNA
      amplification primer

<400> SEQUENCE: 13
```

```
-continued aaatggataa cttcttaccc tttcc                                        25

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:cDNA
      amplification primer

<400> SEQUENCE: 14
cggatgaacc cacgtacg                                                18
```